United States Patent
Imai

[19]

[11] Patent Number: 6,040,489
[45] Date of Patent: Mar. 21, 2000

[54] 1,3-BUTADIENE SEPARATION FROM A CRUDE $C_4$ STREAM USING CATALYTIC EXTRACTIVE DISTILLATION

[75] Inventor: Tamotsu Imai, Mount Prospect, Ill.

[73] Assignee: UOP LLC, Des Plaines, Ill.

[21] Appl. No.: 09/208,232

[22] Filed: Dec. 9, 1998

[51] Int. Cl.[7] ............... C07C 5/03; C07C 5/02; C07C 7/10
[52] U.S. Cl. ............ 585/260; 585/261; 585/264; 585/833; 585/860; 585/864; 203/29; 203/DIG. 6
[58] Field of Search .................. 585/260, 261, 585/264, 833, 860, 864; 203/29, DIG. 6

[56] References Cited

U.S. PATENT DOCUMENTS

| | | | |
|---|---|---|---|
| 3,160,579 | 12/1964 | Fear | 208/143 |
| 3,342,891 | 9/1967 | Poons et al. | 260/681.5 |
| 3,541,178 | 11/1970 | Nettesheim | 260/681.5 |
| 3,842,137 | 10/1974 | Libers et al. | 260/681.5 |
| 3,898,298 | 8/1975 | Desiderio et al. | 260/681.5 |
| 4,277,313 | 7/1981 | Mehra et al. | 203/32 |
| 4,469,907 | 9/1984 | Araki et al. | 585/259 |
| 4,704,492 | 11/1987 | Nemet-Mavrodin | 585/259 |
| 5,414,170 | 5/1995 | McCue et al. | 585/264 |
| 5,877,363 | 3/1999 | Gildert et al. | 585/260 |

FOREIGN PATENT DOCUMENTS

| | | | |
|---|---|---|---|
| 19520389 | 5/1996 | Germany | C07C 11/02 |
| 733030 | 10/1982 | United Kingdom | C07C 7/167 |
| WO 94/04477 | 3/1994 | WIPO | C07C 5/03 |

OTHER PUBLICATIONS

Abrevaya, H; Vora, B.V.; Lentz R.A. "Improved Butadiene Technology for Naphtha Cracking," Presented at the Fifth World Congress of Chemical Engineering, San Diego, Jul. 1996.

*Primary Examiner*—Walter D. Griffin
*Assistant Examiner*—Tam M. Nguyen
*Attorney, Agent, or Firm*—Thomas Kl McBride; Frank S. Molinaro; Maryann Maas

[57] ABSTRACT

A process for separating 1,3-butadiene from a crude $C_4$ stream containing butanes, butenes, butadienes and acetylenes has been developed. The process begins with introducing hydrogen, a solvent, and the crude $C_4$ stream to a catalytic extractive distillation unit having a reaction zone containing a catalyst capable of hydrogenating acetylenes. Butanes and butenes, being less soluble in the solvent, are distilled in an overhead stream from the catalytic extractive distillation unit. Butadienes and acetylenes, being more soluble in the solvent, are carried with the solvent to the reaction zone located within the catalytic extractive distillation unit. In the reaction zone the acetylenes are converted to hydrogenation products. The hydrogenation products other than butadiene are separated from the butadienes by the extractive distillation occurring in the unit. The solvent and butadiene mixture is removed from the catalytic extractive distillation unit in a distillate stream. The distillate stream is then introduced to a solvent stripping column to separate by distillation a solvent bottoms stream from a butadiene overhead stream. The butadiene overhead stream is introduced to a butadiene distillation column to separate a 1,3-butadiene overhead stream from a 1,2-butadiene bottoms stream. The solvent bottoms stream may be purified and recycled to the catalytic distillation unit.

7 Claims, 1 Drawing Sheet

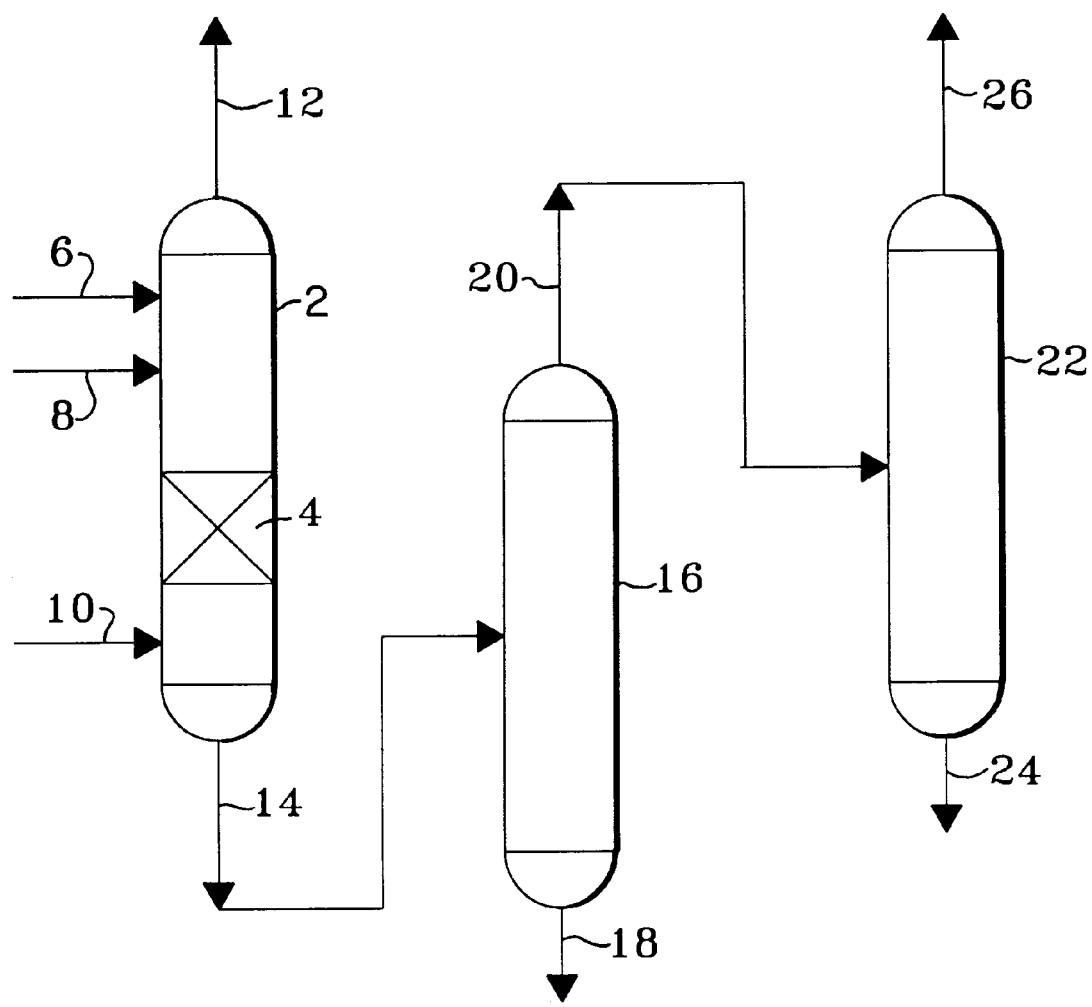

1,3-BUTADIENE SEPARATION FROM A CRUDE $C_4$ STREAM USING CATALYTIC EXTRACTIVE DISTILLATION

BACKGROUND OF THE INVENTION

Butadiene is an important starting material for the production of high molecular weight polymers and is used extensively to form synthetic rubber including styrenebutadiene rubber, nitrile-butadiene rubber, buna-S rubber, and trans-polybutadiene rubber, and adiponitrile and styrene butadiene latex in paints. Butadiene is usually a by-product from steam cracking naphtha and is contained in a crude $C_4$ stream. However, the crude $C_4$ stream regularly contains other hydrocarbons that must be removed before the butadiene may be used as a starting material. The principal components of the crude $C_4$ stream are butanes, butenes, butadienes, and acetylenes including ethylacetylene, methylacetylene and vinylacetylene. Historically, the hydrocarbons are removed from the butadiene in two steps. First the butanes and butenes are removed by extractive distillation using a polar solvent that has greater affinity for unsaturated hydrocarbon compounds than for saturated compounds. Then two different approaches have been used for the removal of acetylenes: extractive distillation using a solvent to selectively absorb the acetylenes or selective hydrogenation of the acetylenes; see Abrevaya, H; Vora, B. V; Lentz, R. A., "Improved Butadiene Technology for Naphtha Cracking," Presented at the Fifth World Congress of Chemical Engineering, San Diego, July 1996. Examples of selective hydrogenation include U.S. Pat. No. 3,342,891, U.S. Pat. No. 3,541,178, U.S. Pat. No. 3,842,137, U.S. Pat. No. 3,898,298, U.S. Pat. No. 4,277,313, U.S. Pat. No. 4,469,907, U.S. Pat. No. 4,704,492, U.S. Pat. No. 5,414,170, and GB 2 040 995.

The patents U.S. Pat. No. 3,541,178, U.S. Pat. No. 3,842,137, U.S. Pat. No. 4,469,907, and U.S. Pat. No. 4,704,492 provide alternate methods of introducing hydrogen to the selective hydrogenation reactor. U.S. Pat. No. 3,342,891 teaches a process of fractionating the butadiene-containing stream into two portions with one portion enriched in acetylenes. Only that portion enriched in acetylenes is subjected to selective hydrogenation. After selective hydrogenation the two portions are recombined. U.S. Pat. No. 5,414,170 discloses a process for selectively hydrogenating the acetylenes in an olefin plant process stream downstream of a front end depropanizer and upstream of further separation zones. U.S. Pat. No. 3,898,298 discloses selective hydrogenation of vinylacetylene using palladium on alumina catalysts at 35° C. and 7 atmospheres to achieve mixed phase operation. GB 2 040 995 discloses admixing a recycle stream and a fresh $C_4$ stream and hydrogenating the mixture, fractionating the product, feeding back an acetylenic stream and recovering butadiene. U.S. Pat. No. 4,277,313 discloses first selectively hydrogenating $C_4$-alkyne components and then using extractive distillation to separate a 1,3-butadiene-rich selective solvent extract phase. Others have used catalytic distillation to concurrently hydrogenate both the dienes and acetylenes; see DE 19520389, EP 733,030, and WO 9404477.

The present invention integrates the two steps of separating the butanes and butenes by extractive distillation and hydrogenating the acetylenes into a single unit by using catalytic extractive distillation. The separation of butanes and butenes from the butadienes is accomplished by extractive distillation, but in the present invention the extractive distillation unit has a reaction zone that contains a catalyst effective for the hydrogenation of acetylenes, hence the term catalytic extractive distillation. The catalyst in the reaction zone is specifically chosen to minimize the hydrogenation of butadienes. As is the case with the butanes and butenes, acetylene hydrogenation products other than butadiene are separated from the butadienes by extractive distillation. Integrating the two steps of the process into a single unit provides a marked reduction in both capital costs and operation costs.

SUMMARY OF THE INVENTION

The purpose of the invention is to provide a process for separating 1,3-butadiene from a crude $C_4$ stream containing butanes, butenes, butadienes and acetylenes. The process begins with introducing hydrogen, a solvent, and the crude $C_4$ stream to a catalytic extractive distillation unit having a reaction zone containing a catalyst capable of hydrogenating acetylenes. Butanes and butenes, being less soluble in the solvent, are distilled in an overhead stream and removed from the catalytic extractive distillation unit. Butadienes and acetylenes, being more soluble in the solvent, are carried with the solvent to the reaction zone located within the catalytic extractive distillation unit. In the reaction zone, the acetylenes are converted to hydrogenation products. The hydrogenation products other than butadiene are separated from the butadienes by the extractive distillation occurring in the unit. The solvent and butadiene mixture is removed from the catalytic extractive distillation unit in an extract stream. The extract stream is then introduced to a solvent stripping column to separate a solvent bottoms stream from a butadiene overhead stream by distillation. The butadiene overhead stream is introduced to a butadiene distillation column to separate a 1,3-butadiene overhead stream from a 1,2-butadiene bottoms stream. The solvent bottoms stream may be purified and recycled to the catalytic distillation unit.

BRIEF DESCRIPTION OF THE DRAWING

The FIGURE is a schematic representation of the separation process of the present invention. The drawing has been simplified by the deletion of a large number of pieces of apparatus customarily employed in processes of this nature which are not specifically required to illustrate the performance of the invention.

DETAILED DESCRIPTION OF THE INVENTION

In general terms, the invention is a cost-efficient process for separating 1,3-butadiene from a crude $C_4$ hydrocarbon stream. Crude $C_4$ streams typically contain butadienes, butenes, butanes, and acetylenes. A small amount of lighter components may also be present. Crude $C_4$ streams may be produced from a variety of sources with the most common being the steam cracking of naptha. The general term "butadienes" is meant to include both 1,2-butadiene and 1,3-butadiene, and the butadienes typically make up from about 35 to about 50 weight percent of the crude $C_4$ feed stream. The butenes are usually present as a mixture of 1-butene and 2-butene, and the butanes are a mixture of normal butane and isobutane. The butenes and butanes together make up from about 40 to 50 weight percent of the crude $C_4$ feed stream. The acetylenes include vinylacetylene, ethylacetylene, and methylacetylene and are frequently from about 0.5 to about 1.5 weight percent of the crude $C_4$ feed stream, but can be as high as 3 weight percent of the crude $C_4$ feed stream. Of the acetylenes, a large portion, usually 75 weight percent, is vinylacetylene.

The crude $C_4$ stream, hydrogen, and a solvent are introduced to a catalytic extractive distillation unit for the separation of butadienes from the other hydrocarbons. The catalytic extractive distillation unit is usually operated at pressures ranging from about 20 psia to about 200 psia or higher and temperatures ranging from about 30° C. (about 85° F.) to about 100° C. (about 220° F.) with the temperatures measured at the selective hydrogenation catalyst bed. Temperatures elsewhere in the catalytic extractive distillation unit, such as at the overhead, may reach to about 150° C. (about 300° F.) or higher. The solvent is typically introduced as an extracting liquid near the top of the column, and the crude $C_4$ stream may be introduced to the unit at a point below that of the solvent. The hydrogen may be introduced at a point below the reaction zone (discussed below). Upon introduction of the crude $C_4$ stream and the solvent, extractive distillation begins to take place. The solvent is chosen to have a higher affinity for unsaturated hydrocarbons than for saturated hydrocarbons. Suitable solvents include dimethylacetamide, dimethylformamide, furfural, N-methyl pyrrolidone, formylmorpholine, and acetonitrile. The less soluble butenes, butanes, and propane and propylene, if present, are distilled away from the solvent and removed in an overhead stream. The more soluble butadienes and acetylenes are carried with the solvent to a reaction zone within the catalytic extractive distillation unit.

The reaction zone contains a catalytic composite effective for the hydrogenation of the acetylenes. Such catalytic composites are known and include composites having copper, one or more Group VIII metals, or a mixture thereof, with a refractory inorganic oxide carrier material. Other activator metals may also be present. Suitable catalysts include those disclosed in U.S. Pat. No. 3,651,167, U.S. Pat. No. 3,912,789, U.S. Pat. No. 4,493,906, U.S. Pat. No. 4,440,956, U.S. Pat. No. 3,751,508 and others. The most preferred catalyst is a composite having copper, nickel, manganese, and cobalt dispersed on a gamma alumina support with a surface area of from about 150 to about 250 $m^2/g$. The reaction zone is operated at a temperature in the range of about 30° C. (about 85° F.) to about 100° C. (about 220° F.). Preferred temperatures for the reaction zone include from about 50° C. (about 120° F.) to about 80° C. (about 180° F.). The temperature is dependent upon the operating pressure. The reaction zone pressure is the same pressure as the catalytic extractive distillation unit operating pressure. It is preferred that the reaction zone be located within the catalytic extractive distillation unit at a position so that some of the butanes and butenes have already been distilled from the solvent, butadienes, and acetylenes mixture. The benefit to such a location is that a reduced volume of fluid is passed through the reaction zone and therefore a reduced amount of catalyst is required.

In the reaction zone, as hydrogen and the crude $C_4$ hydrocarbons contact the catalytic composite, the vinylacetylene is hydrogenated to 1,3-butadiene, the ethylacetylene is hydrogenated to 1-butene, and the methylacetylene is hydrogenated to propylene. The catalytic composite is chosen so that the acetylenes are selectively hydrogenated, and only minimal, if any, butadiene is hydrogenated. Because the reaction zone is located within the catalytic extractive distillation unit, extractive distillation is also occurring within the reaction zone. As the acetylenes are hydrogenated to hydrogenation products, the extractive distillation separation will operate to distill the less soluble propylene and 1-butene into the overhead stream and the more soluble 1,3-butadiene into an extractive distillation column distillate stream containing a mixture of solvent and butadienes. A small amount of unconverted hydrogen can be removed as overhead net gas stream from an overhead condenser of the catalytic extractive distillation column.

The catalytic extractive distillation unit distillate stream, or extract stream, is conducted to a solvent stripping column which is operated at pressures ranging from about 15 psia to about 50 psia and temperatures ranging from about 30° C. (about 85° F.) to about 200° C. (about 400° F.). In this column the solvent is separated from the butadienes. The butadienes are removed in a stripping column overhead stream and the solvent is removed in a stripping column bottoms stream. The stripping column overhead stream is processed further to separate the butadiene isomers for use as a starting material in processes such as the production of synthetic rubber or adiponitrile and styrene-butadiene latex for paint (see below). The stripping column bottoms stream may be conducted to a solvent purification unit where impurities including for example polymeric by-products generated in the reaction zone are removed from the solvent before the solvent is recycled to the catalytic extractive distillation unit.

The stripping column overhead stream is conducted to a butadiene distillation column to distill a 1,3-butadiene overhead stream from a 1,2-butadiene bottoms stream. The butadiene distillation column is operated at pressures ranging from about 30 psia to about 150 psia and temperatures ranging from about 20° C. (about 70° F.) to about 100° C. (about 220° F.). The 1,3-butadiene overhead stream is collected.

Without intending any limitation on the scope of the present invention and as merely illustrative, this invention is explained below in specific terms as applied to a particular embodiment of the invention. Turning now to the FIGURE catalytic extractive distillation column 2 is operated at 84 psia with a receiver temperature of 38° C. (100° F.). Catalytic extractive distillation column 2 has reaction zone 4 which contains a fixed bed of catalytic composite having copper, nickel, manganese, and cobalt dispersed on a gamma alumina support having a surface area of from about 150 to about 250 $m^2/g$. A crude $C_4$ stream, as described above, is introduced to the catalytic extractive distillation column 2 via line 8. Dimethylformamide heated to 60° C. (140° F.) is also introduced to catalytic extractive distillation column 2 as the extractant via line 6. Hydrogen is introduced to extractive distillation column 2 via line 10.

As the crude $C_4$ stream and the solvent enter catalytic extractive distillation column, they mix and extractive distillation begins to occur. The solvent extracts the butadienes and the acetylenes and the extract mixture is carried through catalytic extractive distillation column 2 to reaction zone 4. The nonextracted components including hydrogen, butanes, and butenes are removed from catalytic extractive distillation column 2 in overhead stream 12. As extract mixture contacts the catalytic composite in reaction zone 4, the acetylenes are selectively hydrogenated. Vinylacetylene is hydrogenated to 1,3-butadiene, the ethylacetylene is hydrogenated to 1-butene, and the methylacetylene is hydrogenated to propylene. The hydrogenation products of 1-butene and propylene are distilled away from the solvent and are also removed in overhead stream 12. The 1,3-butadiene produced by the vinylacetylene hydrogenation is extracted with the solvent into the extract mixture. The extract mixture containing solvent and butadienes is removed from catalytic extractive distillation column 2 via line 14.

The extract mixture is conducted through line 14 and introduced to a solvent stripping column 16 operating at 15 psia and 46° C. (115° F.) as measured at the overhead. Butadienes are distilled from the dimethylformamide solvent and removed from solvent stripping column 16 in line 20. The dimethylformamide solvent is removed from solvent stripping column 16 in line 18. The separated solvent may be conducted to a solvent purification unit (not shown) where impurities may be removed. The purified solvent may then be recycled to catalytic extractive distillation column 2.

The butadienes are conducted via line 20 to a butadiene distillation column 22 operating at 65 psia and 46° C. (115° F.) as measured at the overhead. In butadiene distillation column 22, 1,3-butadiene is distilled from 1,2-butadiene. The 1,3-butadiene is removed from the butadiene distillation column via line 26, and the 1,2-butadiene is removed from the butadiene distillation column via line 24. High molecular weight impurities will be removed with the 1,2-butadiene via line 24. The 1,3-butadiene product in line 26 may be collected.

It must be emphasized that the above description is merely illustrative of a preferred embodiment and is not intended as an undue limitation on the generally broad scope of the invention. Moreover, while the description is narrow in scope, one skilled in the art would understand how to extrapolate to the broader scope of the invention. For example, operating at different conditions, using different catalytic composites, and using different solvents can be readily extrapolated from the foregoing description.

What is claimed is:

1. A process for separating 1,3-butadiene from a crude $C_4$ stream containing butanes, butenes, butadienes and acetylenes, said process comprising
    a) introducing hydrogen, a solvent, and the crude $C_4$ stream to a catalytic extractive distillation unit having a reaction zone containing a catalyst capable of hydrogenating acetylenes, to distill an overhead stream containing at least butanes and butenes from an extract stream containing at least solvent and butadienes with concurrent hydrogenation of acetylenes to form hydrogenation products;
    b) introducing the extract stream to a solvent stripping column to distill a solvent bottoms stream from a butadiene overhead stream; and
    c) introducing the butadiene overhead stream to a butadiene distillation column to distill a 1,3-butadiene overhead stream from a 1,2-butadiene bottoms stream.

2. The process of claim 1 where the solvent is selected from the group consisting of dimethylacetamide, dimethylformamide, furfural, N-methyl pyrrolidone, formylmorpholine, and acetonitrile.

3. The process of claim 1 further comprising recycling the solvent bottoms stream to the catalytic extractive distillation unit.

4. The process of claim 1 wherein the catalytic extractive distillation unit is operated at a pressure ranging from about 20 psia to about 200 psia and a temperature ranging from about 30° C. (about 85° F.) to about 150° C. (about 300° F.).

5. The process of claim 1 wherein th catalyst contains copper, one or more Group VIII metals, or a mixture thereof, with a refractory inorganic oxide carrier material.

6. The process of claim 1 wherein the solvent stripping column is operated at a pressure ranging from about 15 psia to about 50 psia and a temperature ranging from about 30° C. (about 85° F.) to about 200° C. (about 400° F.).

7. The process of claim 1 wherein the butadiene distillation column is operated at a pressure ranging from about 30 psia to about 150 psia and a temperature ranging from about 20° C. (about 70° F.) to about 100° C. (about 220° F.).

* * * * *